United States Patent [19]

Mentzer, Jr. et al.

[11] Patent Number: 4,880,783

[45] Date of Patent: Nov. 14, 1989

[54] USE OF ADENOSINE, HYPOXANTHINE AND RIBOSE-CONTAINING SOLUTION FOR IMPROVED PROTECTION OF THE HEART DURING SURGERY

[75] Inventors: Robert M. Mentzer, Jr.; Stephen W. Ely; Robert D. Lasley; Robert M. Berne, all of Charlottesville, Va.

[73] Assignee: University of Virginia Alumnia Patents Foundation, Charlottesville, Va.

[21] Appl. No.: 252,027

[22] Filed: Sep. 29, 1988

Related U.S. Application Data

[63] Continuation of Ser. No. 915,557, Oct. 6, 1986, abandoned.

[51] Int. Cl.$^4$ .............................................. A61K 31/70
[52] U.S. Cl. ...................................... 514/46; 514/45; 514/921; 536/24; 536/26
[58] Field of Search .......................... 514/45, 46, 921; 536/24, 26

[56] References Cited

U.S. PATENT DOCUMENTS

| | | | |
|---|---|---|---|
| 2,994,640 | 8/1961 | Zellner | 424/180 |
| 3,868,451 | 2/1975 | Stein et al. | 424/253 |
| 3,914,414 | 10/1975 | Stein et al. | 424/180 |
| 3,992,531 | 11/1976 | Prasad et al. | 536/24 |
| 4,299,832 | 11/1981 | Brown et al. | 424/253 |
| 4,338,319 | 7/1982 | Kjellin et al. | 424/253 |
| 4,360,522 | 11/1982 | Schaeffer | 544/244 |
| 4,388,308 | 6/1983 | Hamilton et al. | 536/26 |
| 4,415,556 | 11/1983 | Bretschneider | 424/153 |
| 4,473,571 | 9/1984 | Lesher et al. | 424/253 |
| 4,481,197 | 11/1984 | Rideout et al. | 536/26 |
| 4,501,735 | 2/1985 | Trivedi et al. | 514/46 |
| 4,514,405 | 4/1985 | Irmscher et al. | 514/46 |
| 4,544,556 | 10/1985 | Fedi et al. | 473/08 |
| 4,546,095 | 10/1985 | Markov | 514/23 |
| 4,590,180 | 5/1986 | Irmscher et al. | 514/46 |
| 4,593,019 | 6/1986 | Bristol et al. | 514/46 |
| 4,605,644 | 8/1986 | Foker | 514/23 |
| 4,614,732 | 9/1986 | Hamilton et al. | 514/46 |
| 4,673,563 | 6/1987 | Berne et al. | 514/46 |
| 4,693,996 | 9/1987 | Steffen | 514/46 |

OTHER PUBLICATIONS

Schrader et al, "Inhibition of Slow Action Potentials of Guinea Pig A Trial Muscle by Adenosine: A Possible Effect on $Ca^{2+}$ Influx,", Journal of Molecular and Cellular Cardiology (1975) 7, 427–433.

Ely et al, "Functional and Metabolic Evidence of Enhanced Myocardial Tolerance to Ischemia and Reperfusion with Adenosine," J. Thorac Cardiovase Surg. 90:549–556, (1985).

Winn et al, "Incorporation of Adenosine and Its Metabolites into Brain Nucleotides," American Physiological Society (1980), pp. H214–H219.

Wiedmeier et al., "Inosme Incorporation into Myocardial Nucleotides", Journal of Molecular and Cellular Cardiology, 4:445–452 (1972), U.S.A.

Wiedmeier et al., "Incorporation and Turnover of Adenosine-U-$^{14}$C in Perfused Guinea Pig Myocardian", Am. J. Physiology, 223(1): 31–34 (Jul. 1972), U.S.A.

Primary Examiner—Ronald W. Griffin
Attorney, Agent, or Firm—James Creighton Wray

[57] ABSTRACT

The invention relates to an improved cardioplegic solution for reducing ischemic damage to the heart during operations and/or transplantation. The invented solution contains adenosine, hypoxanthine and ribose in addition to the electrolytes contained in standard cardioplegic solutions.

16 Claims, No Drawings

USE OF ADENOSINE, HYPOXANTHINE AND RIBOSE-CONTAINING SOLUTION FOR IMPROVED PROTECTION OF THE HEART DURING SURGERY

This is a continuation of U.S. application Ser. No. 06/915557, filed Oct. 6, 1986 now abandoned.

BACKGROUND OF THE INVENTION

1. Field of the Invention

The present invention relates to an improved cardioplegic solution to protect the heart from ischemia-induced damage incurred during interruption of the blood circulation to the heart during surgery and transplantation.

2. Description of the Prior Art

Surgical procedures for the correction of complex congenital heart abnormalities, placement of cardiac valvular prostheses or repair of defective valves, and bypassing obstructed coronary vessels requires the body to be supported by the heart-lung machine while the heart is rendered quiescent by interruption of its blood supply and briefly perfusing it with a cold solution electrolytes and a high potassium concentration (cardioplegic solution). This enables the surgeon to work in a still and bloodless field to complete the intricate surgical procedures before irreversible ischemic damage is incurred.

The ischemic heart tolerates ischemia for 20-30 minutes before irreversible damage occurs. With the onset of ischemia, the supply of substrates for energy production ceases, and the high energy phosphate adenosine triphosphate (ATP) (which provides energy for contraction and operation of ion pumps in the myocardial cell) is degraded over time to its precursors ADP and AMP. AMP can undergo further degradation at the myocardial membrane to the diffusable purine nucleoside adenosine. Adenosine is also rapidly metabolized to inosine, hypoxanthine and xanthine. With the restoration of blood floow, these nucleosides are washed out of the heart via the circulation. If the ischemia time has been of sufficient length, the level of ATP is reduced, hence less energy for contraction and maintenance of ionic fluxes, and the contractile function of the heart may be diminished or lost. Therefore, methods were developed which would extend the length of time the heart could tolerate ischemia in order to reduce the morbidity and mortality of cardiac operations. Investigations of possible solutions useful in delaying the onset of ischemic damage have involved the use of a multitude of ingredients, but the standard cardioplegic solution in use today contains normal plasma concentrations of electrolytes with the exception of an elevated concentration of potassium which depolarizes the cardiac muscle, rendering it quiescent. The use of hyperkalemic solutions with hypothermia to lower the basal metabolic rate of the cardiac tissue reduces the rate of ATP degradation during ischemia and increases the tolerated ischemic time of the heart during surgery. The protection afforded by these techniques, however, it not optimal in all cases and inadequate myocardial protection during prolonged ischemia is responsible for prolonged weaning from the cardiopulmonary bypass machine, the use of inotropic drugs to support the failing heart postoperatively, and for the mortality associated with postoperative arrhythmias or cardiac failure. Therefore, improvements in the protective cardioplegic solution are needed to reduce the risks attendant with cardiac surgical procedures.

SUMMARY OF PRESENT INVENTION

We have discovered that the measured ability of the myocardium to tolerate ischemia can be enhanced significatly with the addition of adenosine, hypoxanthine and ribose to standard electrolyte solutions. The improved effect can be measured in terms of greater preservation of high energy phosphates during ischemia, more rapid recovery of high energy phosphates after ischemia, and a greater recovery of contractile function following an ischemic period. The use of this solution provides increased protection of the heart during ischemia incurred during surgery, or during the transportation of the heart between donor and recipient for cardiac transplantation.

DESCRIPTION OF THE PREFERRED EMBODIMENT

Adenosine, hypoxanthine and ribose are endogenous substances. Adenosine and hypoxanthine are purine nucleosides; ribose is a sugar. When these substances are used as additives to standard cardioplegic solutions, a relatively high local concentration in the heart can be achieved, without exposure to the systemic circulation. Since these substances are washed out of the myocardium and rapidly distributed and metabolized, they provide a very wide margin of safety.

The rationale behind the use of these substances is to fascilitate the preservation and repletion of the adenine nucleotide pool during ischemia by serving as substrate for the purine nucleotide salvage pathways. These pathways are summarized below.

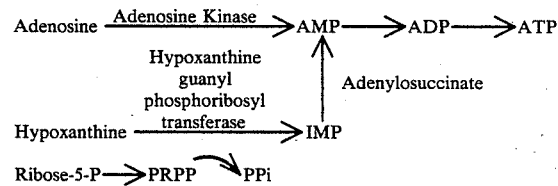

During ischemia, the intracellular adenine nucleotide pool is degraded to the diffusable nucleosides adenosine, inosine and hypoxanthine. These nucleosides are then washed out during the reperfusion period. ATP levels may be depressed for as long as 7-10 days due to the loss of these nucleotide precursors adenosine, inosine, hypoxanthine. The restoration of the adenine nucleotides can be accomplished via two major pathways. The first is via de novo synthesis, however, this pathway is very slow and more than one week would be required to replenish a 50% decline in ATP levels. The second mechanism includes the nucleotide salvage pathways which include the direct phosphorylation of adenosine to AMP, and the phosphorylation of hypoxanthine to IMP which is then converted to AMP. From AMP, ADP and ultimately ATP can be regenerated if irreversible damage of the intracellular organelles has not occurred. The salvaged hypoxanthine requires its condensation with phosphoribosyl-pyrophosphate (PRPP) which in turn is derived from the ribose moiety. Thus, in the absence of damage to the cells' biochemical machinery, the cell is capable of regenerating these high energy phosphate pools (AMP, ADP, ATP) relatively rapidly. Yet in actuality, the restoration of high energy phosphates post-ischemia occurs quite slowly. The retarded rate of recovery may be due to the low concentrations of substrate precursor in the form of adenosine, hypoxanthine and ribose.

The discovery that adenosine and hypoxanthine are individually capable of preserving and/or restoring myocardial ATP was achieved in experiments carried out in the Langendorff isolated perfused rat heart model. Adenosine (100 μM) or hypoxanthine (100 μM) were used in addition to a standard heart perfusate, and the effects on preischemic, ischemic and post-ischemic ATP values were determined and are presented in Table 1.

TABLE 1

| | ATP μmoles/g wet weight | | | | |
|---|---|---|---|---|---|
| | Equilibration | 10' Ischemia | 15' RP | 30' RP | 60' RP |
| Untreated | 3.4 ± 0.1 | 1.2 ± 0.1 | 2.1 ± .07 | 2.1 ± 0.1 | 2.1 ± 0.1 |
| Adenosine | 3.9 ± 0.4 | 1.7 ± 0.1 | 2.9 ± .08 | 2.7 ± .08 | 2.7 ± .06 |
| Untreated | 3.4 ± .1 | 1.4 ± .1 | 2.3 ± .1 | 2.2 ± .1 | 1.8 ± .2 |
| Hypoxanthine | 3.4 ± .2 | 1.4 ± .2 | 2.7 ± .2 | 2.7 ± .1 | 2.3 ± .1 |

RP = reperfusion, N ≧ 5, T = 37° C.

These experiments demonstrated that adenosine or hypoxanthine are able to enhance nucleotide pools (ATP) during ischemia and/or during the post-ischemic reperfusion period. The improvement on energy stores would theoretically improve the functional recovery of the heart since ATP is necessary for contractile activity. This hypothesis was also tested using the aforementioned isolated rat heart model. The effects of adenosine and hypoxanthine on the recovery of cardiac contractile function was assessed by the determination of left ventricular developed pressure during the post-ischemic reperfusion phase with the use of an intra-ventricular saline filled balloon. These results are shown in Table 2.

TABLE 2

| | % of Control Developed Pressure | | | |
|---|---|---|---|---|
| | Control | 15' RP | 30' RP | 60' RP |
| Untreated | 100% | 75 ± 7 | 73 ± 6 | 73 ± 6 |
| Adenosine | 100% | 86 ± 3 | 96 ± 3 | 95 ± 3 |
| Untreated | 100% | 76 ± 5 | 74 ± 5 | 82 ± 5 |
| Hypoxanthine | 100% | 84 ± 5 | 88 ± 2 | 87 ± 3 |

RP = Reperfusion, N ≧ 5, T = 37° C.

These data established that either adenosine or hypoxanthine is capable of restoring the contractile function of the isolated perfused rat heart after a period of 10 minutes of total ischemia.

To extend these studies from an in vitro system to a clinically relevant in vivo model, we compared the effects of a standard cardioplegic electrolyte solution versus the same electrolyte solution with the exception of the addition of adenosine, hypoxanthine and ribose. Using dogs on cardiopulmonary bypass, the same protocol was used as is conventional in clinical cardiac surgery. The animals were anesthetized, placed on the cardiopulminary bypass machine and a saline-filled balloon was inserted into the left ventricle of the heart to record developed pressure. Following stabilization of hemodynamic variables, the hearts were flushed via the native coronary circulation with either a standard cardioplegic solution or the same solution containing adenosine, hypoxanthine and ribose for five minutes prior to the onset of ischemia. The electrolyte contents of these two solutions are shown in Table 3.

TABLE 3

| | Standard Cardioplegic Solution | Invented Cardioplegic Solution |
|---|---|---|
| Na | 110 meq/1 | 110 meq/1 |
| Cl | 160 meq/1 | 160 meq/1 |
| K | 16 meq/1 | 16 meq/1 |
| Ca++ | 2.4 meq/1 | 2.4 meq/1 |
| Mg | 32 meq/1 | 32 meq/1 |
| Ado | 0 | 100 μmoles/1 |
| Hx | 0 | 100 μmoles/1 |
| Ribose | 0 | 2 mmoles/1 |

The pH of each solution was adjusted to 7.4 and the osmolarity was approximately 300 mosom in each. Following cardioplegic arrest, the heart was made ischemic for 1 hour at 37° C. During the hour of ischemia, serial biopsies were obtained to determine the rate of ATP degradation in the untreated and treated group. These results are shown in Table 4.

TABLE 4

| | ATP (μmoles/gm wet weight) | | | | |
|---|---|---|---|---|---|
| | 30' equilibration | 15' ischemia | 30' ischemia | 45' ischemia | 60' ischemia |
| Untreated (Std cardioplegia) | 5.09 ± .24 | 3.67 ± .24 | 3.01 ± .25 | 2.03 ± .30 | 1.97 ± .13 |
| Treated (Std cardioplegia + Adenosine, Hypoxanthine, Ribose) | 5.29 ± .20 | 4.51 ± .34 | 4.03 ± .42 | 3.07 ± .48 | 2.74 ± .27 |

N ≧ 5 in each group

These data show that our invented cardioplegia solution reduces the rate of ATP degradation during ischemia. This finding applied to hearts undergoing conventional cardiac surgical protocols and hearts harvested for cardiac transplantation.

During the post-ischemic reperfusion period, the recovery of ATP pools and the recovery of left heart contractile function were also assessed in the dog model described above. The effects of ischemia on the heart protected with the standard cardioplegic solution were compared to the hearts protected with the same solution except for the addition of adenosine, hypoxanthine and ribose. These results, expressed in terms of recovery of ATP and left heart function, are shown in Table 5.

TABLE 5

| ATP | | |
|---|---|---|
| μmoles/gm wet weight | | |
| 15' RP | 30' RP | 60' RP |

TABLE 5-continued

ATP

| | | | |
|---|---|---|---|
| Untreated (Std solution) | 2.77 ± .22 | 2.13 ± .21 | 2.95 ± .16 |
| Treated (Std solution + Adenosine, Hypoxanthine, Ribose) | 3.24 ± .39 | 3.22 ± .32 | 3.33 ± .33 |

| | % Recovery of Developed Pressure | | | |
|---|---|---|---|---|
| | 15' RP | 30' RP | 45' RP | 60' RP |
| Untreated (Std solution) | 19 ± 3.0 | 27 ± 3.2 | 42 ± 1 | 49 ± 3 |
| Treated (Std solution + Adenosine, Hypoxantine, Ribose) N ≧ 5 | 25 ± 4 | 40 ± 4 | 54 ± 3 | 67 ± 4 |

These experiments show that the protection of the heart during one hour of ischemia at 37° C. is greater in terms of preservation and recovery of ATP levels and in terms of recovery of the contractile function of the heart when the invented soluton containing adenosine, hypoxanthine and ribose is compared to a standard clinically accepted cardioplegic solution.

Preferably, the invention is embodied in:

(1) A formula for the preparation of a solution for reducing ischemic damage to the heart during cardiac surgery or during harvesting for cardiac transplantation. This solution has the following ionic content:

| | |
|---|---|
| Na | 110 meq/l |
| Cl | 160 meq/l |
| K | 16 meq/l |
| $Ca^{++}$ | 2.4 meq/l |
| Mg | 32 meq |

Adenosine in quantity to yield a final conc. of 100 μmoles/l Hypoxanthine in quantity to yield a final conc. of 100 μmoles/l Ribose in quantity to yield a final conc. of 2 mmoles/l+NaHCO₃ or HCl to adjust pH to 7.4

The above solution represents an improvement over a standard cardioplegic solution due to the addition of adenosine, hypoxanthine and ribose.

(2) A method for reducing ischemic damage to the heart during operations or transplantation by the use of the above invented solution as an infusion to arrest the heart prior to ischemia during operations or prior to harvesting hearts from donors in preparation for transplantation.

We claim:

1. A heart perfusate for reducing ischemic damage to a heart isolated from a normal blood supply comprising a cardioplegic solution having at least one purine nucleoside additive.

2. The cardioplegic solution of claim 1 wherein the additive is adenosine.

3. The cardioplegic solution of claim 1 wherein the additive is adenosine in a final concentration in the solution of about 100 μmoles per liter.

4. The cardioplegic solution of claim 1 wherein the additive is hypoxanthine.

5. The cardioplegic solution of claim 1 wherein the additive is hypoxanthine in a final concentration in the solution of about 100 μmoles per liter.

6. The cardioplegic solution of claim 1 and a sugar additive, wherein the sugar additive is ribose.

7. The cardioplegic solution of claim 1 and a sugar additive, wherein the sugar additive is ribose in a final concentration in the solution of about 2 mmolar.

8. The cardioplegic solution of claim 1 wherein the additive is adenosine, hypoxanthine and ribose.

9. The cardioplegic solution of claim 1 wherein the additive is adenosine in a final concentration in the solution of about 100 μmoles per liter, hypoxanthine in a final concentration in the solution of about 100 μmoles per liter, and ribose in a final concentration in the solution of about 2 mmoles per liter.

10. The cardioplegic solution of claim 1 wherein the additive is adenosine ina final concentration in the solution of about 100 μmoles per liter, hypoxanthine in a final concentration in the solution of about 100 μmoles per liter, and ribose in a final concentration in the solution of about 2 mmoles per liter, further comprising Na, Cl, K, Ca and Mg ions in solution.

11. The cardioplegic solution of claim 1 wherein the additive is adenosine in a final concentration in the solution of about 100 μmoles per liter, hypoxanthine in a final concentration in the solution of about 100 μmoles per liter, and ribose in a final concentration in the solution of about 2 mmoles per liter, further comprising Na, Cl, K, Ca and Mg ions in solution in the following approximate concentrations:

| | |
|---|---|
| Na | 110 meq/l |
| Cl | 160 meq/l |
| K | 16 meq/l |
| $Ca^{++}$ | 2.4 meq/l |
| Mg | 32 meq, and |
| NaHCO₃ or HCl to adjust pH to 7.4. | |

12. An improved method for enhancing ability of a myocardium to tolerate ischemia comprising perfusing a preischemic heart with a cardioplegic solution containing at least one purine nucleoside during either cardiovascular surgery or harvesting for cardiac transplantation, wherein the cardioplegic solution reduces the rate of ATP degradation during ischemia.

13. The method of claim 12 wherein the purine nucleoside is adenosine.

14. The method of claim 12 wherein the purine nucleoside is hypoxanthine.

15. The method of claim 14 further comprising perfusing the heart with a solution containing ribose.

16. The method of claim 12 wherei the at least one purine nucleoside is adenosine and hypoxanthine and wherein the solution further contains ribose.

* * * * *